US00PP12946P2

(12) United States Plant Patent
Hanes

(10) Patent No.: US PP12,946 P2
(45) Date of Patent: Sep. 10, 2002

(54) GERANIUM PLANT NAMED 'FREE WHITE'

(75) Inventor: Mitchell Eugene Hanes, Morgan Hill, CA (US)

(73) Assignee: Goldsmith Plants Inc., Gilroy, CA (US)

( * ) Notice: Subject to any disclaimer, the term of this patent is extended or adjusted under 35 U.S.C. 154(b) by 39 days.

(21) Appl. No.: 09/802,866

(22) Filed: Mar. 12, 2001

(51) Int. Cl.[7] ..... A01H 5/00
(52) U.S. Cl. ..... Plt./332
(58) Field of Search ..... Plt./332, 324, 325

*Primary Examiner*—Bruce R. Campell
*Assistant Examiner*—June Hwu
(74) *Attorney, Agent, or Firm*—Rothwell, Figg, Ernst & Manbeck

(57) ABSTRACT

A geranium cultivar particularly distinguished by green foliage, white flower color, and semi-double flowers on large umbels, fast rooting and exhibits vigorous growth.

1 Drawing Sheet

GENUS AND SPECIES

*Pelargonium hortorum.*

VARIETY DENOMINATION

Figure 1:
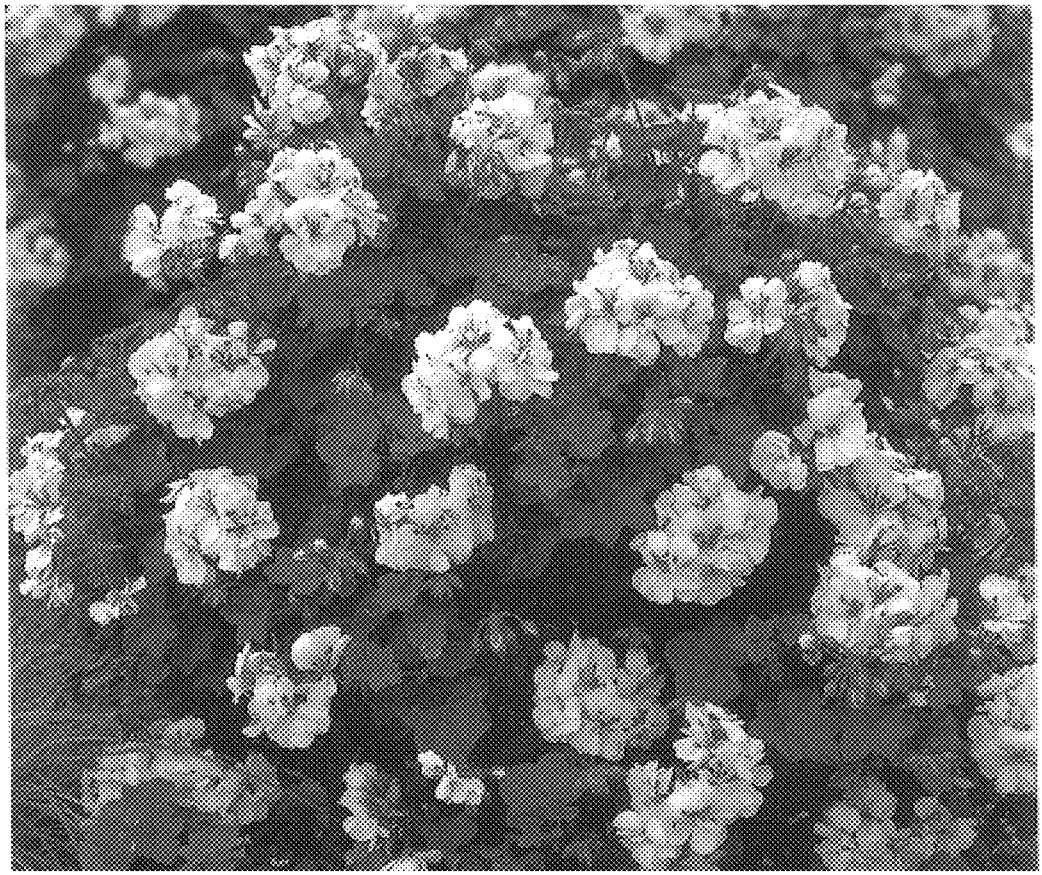

'Free White'.

BACKGROUND OF THE NEW PLANT

The present invention comprises a new and distinct cultivar of geranium, botanically known as *Pelargonium peltatum* Bailey, and hereinafter referred to by the cultivar name 'Free White'. The new cultivar is propagated from a seedling resulting from the cross of 7407-2 a white flowered, unnamed and unpatented proprietary line and 6745-3 a white flowered, unnamed and unpatented proprietary line.

'Free White' is a product of a planned breeding program intended to create new geranium cultivars with white colored flowers, semi-double flower form, green foliage, vigorous growth and superior cutting productivity.

The new cultivar was created in 1997 in Gilroy, Calif. and has been repeatedly asexually reproduced by cuttings in Gilroy, Calif. and Guatemala over a two and a half year period. It has also been trialed at Gilroy, Calif. and Andijk, The Netherlands. It has been found to retain its distinctive characteristics through successive propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit.

DESCRIPTION OF THE NEW CULTIVAR

The following detailed descriptions set forth the distinctive characteristics of 'Free White'. The data which defines these characteristics were collected from asexual reproductions carried out in Gilroy, Calif. The plant history was taken on five month old plants grown in 8 inch pots, blossomed under natural light in a greenhouse and color readings were taken in the greenhouse in Gilroy, Calif. Color references are primarily to The R.H.S. Colour Chart of The Royal Horticultural Society of London (R.H.S.).

DETAILED BOTANICAL DESCRIPTION

Classification:
*Botanical.*—*Pelargonium peltatum.*
*Commercial.*—Ivy Geranium.
Form: Upright, yet trailing, spreading.
Height:
*From soil level to top of plant* (*excluding blooms*).—13 cm.
*From soil level to top of umbels.*—24 cm.
Width: 65 cm; if lateral branches are outstretched the width is 90 cm.
Time to produce a finished flowering plant: 13 weeks.
Outdoor plant performance: Good weather tolerance, strong growth.
Time to initiate roots: 7–8 days.
Time to develop roots: 25 days.
Root description: White, slightly pubescent, fibrous yet coarse.

The Leaves

Length: 4.5–7.0 cm.
Width: 6.0–9.5 cm depending on age.
Apex description: Acute.
Base description: Cordate, two bottom lobes are sagitate.
Shape: Peltate, 7 lobed with acute apice.
Margin: Entire, ciliate.
Texture: Lightly pubescent, somewhat succulent.
Ribs and veins: Palmate, 4.0–4.5 cm long.
Color:
*Upper side.*—Yellow-green RHS 146A with a darker zone of 0.5 to 1 cm in width in the center of the leaf that is brown RHS 166B.
*Under side.*—Yellow-green RHS 146B.
*Ribs.*—Yellow-green RHS 146C.
*Veins.*—Yellow-green RHS 146C.
Petiole length: 4.0–7.0 cm depending on age of the leaf.
Petiole diameter: 1.0–2.0 mm.
Petiole color: Yellow-green RHS 144A.

Lateral branch length: 23.5–42.0 cm.
Internode length:
*On young growth.*—2.0–4.0 cm.
*On older growth.*—5.0–7.0 cm.
Lateral branch color: Yellow-green RHS 144A.

The Bud

Diameter: 7.0–8.0 mm.
Length: 1.6–1.8 cm.
Shape: Elliptic.
Color when sepals first divide: White RHS 155D with areas of light green RHS 150D.
Number of sepals: 5–6.
Length of sepals: 1.6–1.8 cm.
Width of sepals: 4.0–6.0 mm.
Apex description: Cuspidate.
Base description: Truncate.
Sepal color in an open flower: Upper and lower are yellow-green RHS 146B.

The Flower

Bloom season: Continuous throughout the year in greenhouse or Zone 9 climate.
Size: Approximately 5.0–6.0 cm in diameter.
Form: Polypetalous, semi-double shape.
Petals/petaloids: 11–14 imbricate petals, 1–3 petaloids; Shape: spatulate.
Apex shape: obtuse.
Base shape: Attenuate.
Margin: Entire, slightly undulating (serrulate).
Upper petal/petaloid color:
*Upper petal surface.*—White RHS 155D with a macule and 2 vertical stripes approximately 2 cm in length extending from the macule to the petal base with a color of dark pink RHS 66A.
*Petal under surface.*—White RHS 155D with stripes approximately 2 cm in length that are dark pink RHS 66A.
*Petaloid color.*—Upper surface is white RHS 155D with stripes of dark pink RHS 66B and lower surface—white RHS 155D with very faint stripes of dark pink RHS 66B–C.
Surface texture: Papillose (Satiny).
Lowerpetal/petaloid color: Upper petal color is white RHS 155D with very faint stripes of dark pink RHS 66B and 66C; underside of petals is white RHS 155D. Upper petaloid color is white RHS 155D with stripes of dark pink RHS 66B; and underside is white RHS 155D.
Color change with age: May turn slightly pink RHS 69C with age or cool night temperatures.
Pedicel length: Approximately 3.0–3.4 cm.
Pedicel color: Yellow-green RHS 144A.
Flower persistence: An open flower will hold it's petals until the flower begins to dehisce, or approximately 7–10 days.

The Inflorescence

Type: An umbel composed of approximately 7 flowers.
Diameter: 8.0–10.0 cm.
Depth: 5.5 cm.
Peduncle length: 11.0–11.5 cm.
Peduncle color: Yellow-green RHS 144A.

The Reproductive Organs

Anthers: 7–8.
Anther color: Red-purple RHS 60C prior to anthesis.
Filament color: Dark pink RHS 69A.
Lengths of anthers and filaments: Anther— 0.3 cm; filament 1.2–1.7 cm.
Pollen amount and color: Moderate orange RHS 25A.
Pistil: 1 with a length of 1.0 cm.
Stigma: 5 linear lobes with a color of pink RHS 66C.
Style: 4.0 mm with a color of white RHS 155D.
Ovary: At anthesis, densely pubescent with white hairs, oblong, green drying to a light brown at maturity.
Seed number: Maximum of 5 per spike.
Seed length: 4–5 mm.
Seed width: 1.0–1.5 mm.
Seed color: Grey-orange RHS 177B that may darken with age.

Disease and Insect Resistance

No susceptibility to diseases or insects noted to date.

Comparison with Known Cultivars

'Free White' has a more branched, controlled spreading habit than 7407-2 and has a more vigorous, weather resistant growth than 6745-3.

I claim:

1. A new and distinct cultivar of geramium plant as shown and described herein.

* * * * *